(12) United States Patent
Folkerts et al.

(10) Patent No.: US 11,090,508 B2
(45) Date of Patent: *Aug. 17, 2021

(54) SYSTEM AND METHOD FOR BIOLOGICAL TREATMENT PLANNING AND DECISION SUPPORT

(71) Applicants: Varian Medical Systems, Palo Alto, CA (US); Varian Medical Systems International AG, Cham (CH); Varian Medical Systems Particle Therapy GmbH & Co. KG, Troisdorf (DE)

(72) Inventors: Michael Matthew Folkerts, Carrollton, TX (US); Jessica Perez, Geneva (CH); Christel Smith, Santa Barbara, CA (US); Eric Abel, San Jose, CA (US); Anthony Magliari, Newark, IL (US); Reynald Vanderstraeten, Uccle (BE); Timo Kalevi Koponen, Espoo (FI); Renate Parry, Oakland, CA (US); Alexander Katsis, San Mateo, CA (US); Rajiv Dua, Manteca, CA (US); Michiko Alcanzare, Espoo (FI); Perttu Niemela, Espoo (FI); Matti Ropo, Turku (FI)

(73) Assignees: Varian medical Systems Particle Therapy GmbH & Co. KG, Troisdorf (DE); Varian Medical Systems International AG, Cham (CH); Varian Medical Systems, Inc., Palo Alto, CA (US)

( * ) Notice: Subject to any disclaimer, the term of this patent is extended or adjusted under 35 U.S.C. 154(b) by 147 days.

This patent is subject to a terminal disclaimer.

(21) Appl. No.: 16/297,448

(22) Filed: Mar. 8, 2019

(65) Prior Publication Data
US 2020/0282233 A1  Sep. 10, 2020

(51) Int. Cl.
*A61N 5/10* (2006.01)
*G06T 7/00* (2017.01)

(52) U.S. Cl.
CPC ......... *A61N 5/1031* (2013.01); *A61N 5/1037* (2013.01); *A61N 5/1039* (2013.01);
(Continued)

(58) Field of Classification Search
CPC .. A61N 5/1031; A61N 5/1039; A61N 5/1037; A61N 2005/1074;
(Continued)

(56) References Cited

U.S. PATENT DOCUMENTS

| 6,222,544 B1 | 4/2001 | Tarr et al. |
| 6,260,005 B1 | 7/2001 | Yang et al. |

(Continued)

FOREIGN PATENT DOCUMENTS

| CN | 104001270 | 8/2014 |
| CN | 106730407 | 5/2017 |

(Continued)

OTHER PUBLICATIONS

Schell S et al., "Radiobiological Effect Based Treatment Plan Optimization with the linear Quadratic Model", Zeitschrift Fuer Mediziniche Physik. Urban and Fischer, Aug. 2, 2010 (Aug. 1, 2010), pp. 188-196, vol. 20, No, 3, Jena, DE.

(Continued)

*Primary Examiner* — Don K Wong

(57) ABSTRACT

Embodiments of the present invention provide an integrated solution to radiotherapy treatment planning that enables accurate recording and accumulation of physical parameters as input (e.g., dose, dose rate, irradiation time per voxel, etc.). User-defined functions are evaluated to correlate the input parameters with 4D biological outcomes. The resulting biological parameters can be visualized as a biological (Continued)

outcome map to evaluate decisions, support decisions, and optimize decisions regarding the parameters of the radiotherapy treatment plan, for example, for supporting clinical trials and related clinical research.

28 Claims, 3 Drawing Sheets

(52) U.S. Cl.
CPC .......... *A61N 5/1038* (2013.01); *A61N 5/1071* (2013.01); *A61N 2005/1041* (2013.01); *A61N 2005/1074* (2013.01)

(58) Field of Classification Search
CPC .......... A61N 2005/1041; A61N 5/1038; A61N 5/1071; A61N 5/103; A61B 2034/107; A61B 34/10; A61B 5/7246; A61B 90/37
See application file for complete search history.

(56) References Cited

U.S. PATENT DOCUMENTS

| | | |
|---|---|---|
| 6,379,380 B1 | 4/2002 | Satz |
| 6,411,675 B1 | 6/2002 | Llacer |
| 6,504,899 B2 | 1/2003 | Pugachev et al. |
| 6,993,112 B2 | 1/2006 | Hesse |
| 7,268,358 B2 | 9/2007 | Ma et al. |
| 7,453,983 B2 | 11/2008 | Schildkraut et al. |
| 7,515,681 B2 | 4/2009 | Ebstein |
| 7,560,715 B2 | 7/2009 | Pedroni |
| 7,590,219 B2 | 9/2009 | Maurer, Jr. et al. |
| 7,616,735 B2 | 11/2009 | Maciunas et al. |
| 7,623,623 B2 | 11/2009 | Raanes et al. |
| 7,778,691 B2 | 8/2010 | Zhang et al. |
| 7,807,982 B2 | 10/2010 | Nishiuchi et al. |
| 7,831,289 B2 | 11/2010 | Riker et al. |
| 7,835,492 B1 | 11/2010 | Sahadevan |
| 8,401,148 B2 | 3/2013 | Lu et al. |
| 8,406,844 B2 | 3/2013 | Ruchala et al. |
| 8,559,596 B2 | 10/2013 | Thomson et al. |
| 8,600,003 B2 | 12/2013 | Zhou et al. |
| 8,613,694 B2 | 12/2013 | Walsh |
| 8,636,636 B2 | 1/2014 | Shukla et al. |
| 8,644,571 B1 | 2/2014 | Schulte et al. |
| 8,716,663 B2 | 5/2014 | Brusasco et al. |
| 8,847,179 B2 | 9/2014 | Fujitaka et al. |
| 8,948,341 B2 | 2/2015 | Beckman |
| 8,986,186 B2 | 3/2015 | Zhang et al. |
| 8,995,608 B2 | 3/2015 | Zhou et al. |
| 9,018,603 B2 | 4/2015 | Loo et al. |
| 9,033,859 B2 | 5/2015 | Fieres et al. |
| 9,149,656 B2 | 10/2015 | Tanabe |
| 9,155,908 B2 | 10/2015 | Meltsner et al. |
| 9,233,260 B2 | 1/2016 | Slatkin et al. |
| 9,283,406 B2 | 3/2016 | Prieels |
| 9,308,391 B2 | 4/2016 | Liu et al. |
| 9,333,374 B2 | 5/2016 | Iwata |
| 9,517,358 B2 | 12/2016 | Velthuis et al. |
| 9,545,444 B2 | 1/2017 | Strober et al. |
| 9,636,381 B2 | 5/2017 | Basile |
| 9,636,525 B1 | 5/2017 | Sahadevan |
| 9,649,298 B2 | 5/2017 | Djonov et al. |
| 9,656,098 B2 | 5/2017 | Goer |
| 9,694,204 B2 | 7/2017 | Hardemark |
| 9,776,017 B2 | 10/2017 | Flynn et al. |
| 9,786,093 B2 | 10/2017 | Svensson |
| 9,795,806 B2 | 10/2017 | Matsuzaki et al. |
| 9,884,206 B2 | 2/2018 | Schulte et al. |
| 9,931,522 B2 | 4/2018 | Bharadwaj et al. |
| 9,962,562 B2 | 5/2018 | Fahrig et al. |
| 9,974,977 B2 | 5/2018 | Lachaine et al. |
| 9,987,502 B1 | 6/2018 | Gattiker et al. |
| 10,007,961 B2 | 6/2018 | Grudzinski et al. |
| 10,071,264 B2 | 9/2018 | Liger |
| 10,092,774 B1 | 10/2018 | Vanderstraten et al. |
| 10,183,179 B1 | 1/2019 | Smith et al. |
| 10,206,871 B2 | 2/2019 | Lin et al. |
| 10,232,193 B2 | 3/2019 | Iseki |
| 10,258,810 B2 | 4/2019 | Zwart et al. |
| 10,279,196 B2 | 5/2019 | West et al. |
| 10,307,614 B2 | 6/2019 | Schnarr |
| 10,315,047 B2 | 6/2019 | Glimelius et al. |
| 10,413,755 B1 | 9/2019 | Sahadevan |
| 10,525,285 B1 | 1/2020 | Friedman |
| 10,549,117 B2 | 2/2020 | Vanderstraten et al. |
| 10,603,514 B2 | 3/2020 | Grittani et al. |
| 10,609,806 B2 | 3/2020 | Roecken et al. |
| 10,661,100 B2 | 5/2020 | Shen |
| 10,702,716 B2 | 7/2020 | Heese |
| 2007/0287878 A1 | 12/2007 | Fantini et al. |
| 2009/0234626 A1 | 9/2009 | Yu et al. |
| 2009/0264728 A1* | 10/2009 | Fischer .................. A61N 5/103 600/407 |
| 2010/0086183 A1* | 4/2010 | Vik ....................... A61N 5/1031 382/128 |
| 2010/0178245 A1 | 7/2010 | Arnsdorf et al. |
| 2011/0006224 A1 | 1/2011 | Maltz et al. |
| 2011/0091015 A1 | 4/2011 | Yu et al. |
| 2011/0106749 A1 | 5/2011 | Krishnan et al. |
| 2012/0157746 A1 | 6/2012 | Meltsner et al. |
| 2012/0171745 A1 | 7/2012 | Itoh |
| 2013/0231516 A1 | 9/2013 | Loo et al. |
| 2014/0275706 A1 | 9/2014 | Dean et al. |
| 2015/0011817 A1 | 1/2015 | Feng |
| 2015/0202464 A1 | 7/2015 | Brand et al. |
| 2015/0306423 A1 | 10/2015 | Bharat et al. |
| 2016/0279444 A1 | 9/2016 | Schlosser |
| 2016/0310764 A1 | 10/2016 | Bharadwaj et al. |
| 2017/0189721 A1 | 7/2017 | Sumanaweera et al. |
| 2017/0203129 A1 | 7/2017 | Dessy |
| 2017/0281973 A1 | 10/2017 | Allen et al. |
| 2018/0021594 A1 | 1/2018 | Papp et al. |
| 2018/0043183 A1 | 2/2018 | Sheng et al. |
| 2018/0056090 A1 | 3/2018 | Jordan et al. |
| 2018/0099154 A1 | 4/2018 | Prieels |
| 2018/0099155 A1 | 4/2018 | Prieels et al. |
| 2018/0099159 A1 | 4/2018 | Forton et al. |
| 2018/0154183 A1 | 6/2018 | Sahadevan |
| 2018/0197303 A1 | 7/2018 | Jordan et al. |
| 2018/0236268 A1 | 8/2018 | Zwart et al. |
| 2019/0022407 A1 | 1/2019 | Abel et al. |
| 2019/0022411 A1* | 1/2019 | Parry ................... A61N 5/1042 |
| 2019/0022422 A1 | 1/2019 | Trail et al. |
| 2019/0054315 A1 | 2/2019 | Isola et al. |
| 2019/0070435 A1 | 3/2019 | Joe Anto et al. |
| 2019/0168027 A1 | 6/2019 | Smith et al. |
| 2019/0255361 A1 | 8/2019 | Mansfield |
| 2019/0299027 A1 | 10/2019 | Fujii et al. |
| 2019/0299029 A1 | 10/2019 | Inoue |
| 2019/0351259 A1 | 11/2019 | Lee et al. |
| 2020/0001118 A1 | 1/2020 | Snider, III et al. |
| 2020/0022248 A1 | 1/2020 | Yi et al. |
| 2020/0030633 A1 | 1/2020 | Van Heteren et al. |
| 2020/0035438 A1 | 1/2020 | Star-Lack et al. |
| 2020/0069818 A1 | 3/2020 | Jaskula-Ranga et al. |
| 2020/0164224 A1 | 5/2020 | Vanderstraten et al. |
| 2020/0178890 A1 | 6/2020 | Otto |
| 2020/0197730 A1 | 6/2020 | Safavi-Naeini et al. |
| 2020/0254279 A1 | 8/2020 | Ohishi |
| 2020/0269068 A1 | 8/2020 | Abel et al. |
| 2020/0276456 A1 | 9/2020 | Swerdloff |
| 2020/0282234 A1 | 9/2020 | Folkerts et al. |

FOREIGN PATENT DOCUMENTS

| | | |
|---|---|---|
| CN | 107362464 | 11/2017 |
| CN | 109966662 | 7/2019 |
| CN | 111481840 | 8/2020 |
| CN | 111481841 | 8/2020 |
| EA | 010207 | 6/2008 |
| EP | 0979656 | 2/2000 |
| EP | 3338858 | 6/2018 |
| EP | 3384961 | 10/2018 |

(56) References Cited

FOREIGN PATENT DOCUMENTS

| | | |
|---|---|---|
| EP | 3421087 | 1/2019 |
| EP | 3453427 | 3/2019 |
| EP | 3586920 | 1/2020 |
| JP | 2617283 | 6/1997 |
| JP | 2019097969 | 6/2019 |
| WO | 2007017177 | 2/2007 |
| WO | 2010018476 | 2/2010 |
| WO | 2013081218 | 6/2013 |
| WO | 2013133936 | 9/2013 |
| WO | 2014139493 | 9/2014 |
| WO | 2014169744 | 10/2014 |
| WO | 2015038832 | 3/2015 |
| WO | 2015102680 | 7/2015 |
| WO | 2016122957 | 8/2016 |
| WO | 2017156316 | 9/2017 |
| WO | 2017174643 | 10/2017 |
| WO | 2018137772 | 8/2018 |
| WO | 2018152302 | 8/2018 |
| WO | 2019097250 | 5/2019 |
| WO | 2019103983 | 5/2019 |
| WO | 2019164835 | 8/2019 |
| WO | 2019166702 | 9/2019 |
| WO | 2019185378 | 10/2019 |
| WO | 2019222436 | 11/2019 |
| WO | 2020018904 | 1/2020 |
| WO | 2020064832 | 4/2020 |
| WO | 2020107121 | 6/2020 |
| WO | 2020159360 | 8/2020 |

OTHER PUBLICATIONS

Aafke Christine Kraan, "Range verification methods in particle therapy: underlying physics and Monte Carlo modeling," Frontiers in Oncology, Jul. 7, 2015, vol. 5, Article 150, 27 pages, doi: 10.3389/fonc.2015.00150.

Wayne D. Newhauser et al., "The physics of proton therapy," Physics in Medicine & Biology, Mar. 24, 2015, 60 R155-R209, Institute of Physics and Engineering in Medicine, IOP Publishing, doi: 10.1088/0031-9155/60/8/R155.

S E McGowan et al., "Treatment planning optimisation in proton therapy," Br J Radiol, 2013, 86, 20120288, The British Institute of Radiology, 12 pages, DOI: 10.1259.bjr.20120288.

Steven Van De Water et al., "Towards FLASH proton therapy: the impact of treatment planning and machine characteristics on achievable dose rates," Acta Oncologica, Jun. 26, 2019, vol. 58, No. 10, p. 1462-1469, Taylor & Francis Group, DOI: 10.1080/0284186X2019.1627416.

J. Groen, "FLASH optimisation in clinical Impt treatment planning," MSc Thesis, Jul. 1, 2020, Erasmus University Medical Center, department of radiotherapy, Delft University of Technology, 72 pages.

Muhammad Ramish Ashraf et al., "Dosimetry for Flash Radiotherapy: A Review of Tools and the Role of Radioluminescence and Cherenkov Emission," Frontiers in Oncology, Aug. 21, 2020, vol. 8, Article 328, 20 pages, doi: 10.3389/fphy.2020.00328.

Emil Schuler et al., "Experimental Platform for Ultra-high Dose Rate FLASH Irradiation of Small Animals Using a Clinical Linear Accelerator," International Journal of Radiation Oncology, Biology, Physics, vol. 97, No. 1, Sep. 2016, pp. 195-203.

Elette Engels et al., "Toward personalized synchrotron microbeam radiation therapy," Scientific Reports, 10:8833, Jun. 1, 2020, 13 pages, DOI: https://doi.org/10.1038/s41598-020-65729-z.

P-H Mackeprang et al., "Assessing dose rate distributions in VMAT plans" (Accepted Version), Accepted Version: https://boris.unibe.ch/92814/8/dose_rate_project_revised_submit.pdf Published Version: 2016, Physics in medicine and biology, 61(8), pp. 3208-3221. Institute of Physics Publishing IOP, published Mar. 29, 2016, https://boris.unibe.ch/92814/.

Xiaoying Liang et al., "Using Robust Optimization for Skin Flashing in Intensity Modulated Radiation Therapy for Breast Cancer Treatment: A Feasibility Study," Practical Radiation Oncology, vol. 10, Issue 1, p. 59-69, Published by Elsevier Inc., Oct. 15, 2019.

Alexei Trofimov et al., "Optimization of Beam Parameters and Treatment Planning for Intensity Modulated Proton Therapy," Technology in Cancer Research & Treatment, vol. 2, No. 5, Oct. 2003, p. 437-4-44, Adenine Press.

Vladimir Anferov, "Scan pattern optimization for uniform proton beam scanning," Medical Physics, vol. 36, Issue 8, Aug. 2009, pp. 3560-3567, First published: Jul. 2, 2009.

Ryosuke Kohno et al., "Development of Continuous Line Scanning System Prototype for Proton Beam Therapy," International Journal of Particle Therapy, Jul. 11, 2017, vol. 3, Issue 4, p. 429-438, DOI: 10.14338/IJPT-16-00017.1.

Wenbo Gu et al., "Integrated Beam Orientation and Scanning—Spot Optimization in Intensity Modulated Proton Therapy for Brain and Unilateral Head and Neck Tumors," Med Phys. Author manuscript; available in PMC 2019 Apr 1. https://www.ncbi.nlm.nih.gov/pmc/articles/PMC5904040/ Published in final edited form as: Med Phys. Apr. 2018; 45(4): 1338-1350. Published online Mar. 1, 2018. doi: 10.1002/mp.12788 Accepted manuscript online: Feb. 2, 2018.

Paul Morel et al., "Spot weight adaptation for moving target in spot scanning proton therapy," Frontiers in Oncology, May 28, 2015, vol. 5, Article 119, 7 pages, doi: 10.3389/fonc.2015.00119.

Simeon Nill et al., "Inverse planning of intensity modulated proton therapy," Zeitschrift fur Medizinische Physik, vol. 14, Issue 1, 2004, pp. 35-40, https://doi.org/10.1078/0939-3889-00198.

A. Lomax, "Intensity modulation methods for proton radiotherapy," Physics in Medicine & Biology, Jan. 1999, vol. 44, No. 1, pp. 185-205, doi: 10.1088/0031-9155/44/1/014.

M Kramer et al., "Treatment planning for heavy-ion radiotherapy: physical beam model and dose optimization," Physics in Medicine & Biology, 2000, vol. 45, No. 11, pp. 3299-3317, doi: 10.1088/0031-9155/45/11/313.

Harald Paganetti, "Proton Beam Therapy," Jan. 2017, Physics World Discovery, IOP Publishing Ltd, Bristol, UK, 34 pages, DOI: 10.1088/978-0-7503-1370-4.

Shinichi Shimizu et al., "A Proton Beam Therapy System Dedicated to Spot-Scanning Increases Accuracy with Moving Tumors by Real-Time Imaging and Gating and Reduces Equipment Size," PLoS ONE, Apr. 18, 2014, vol. 9, Issue 4, e94971, https://doi.org/10.1371/journal.pone.0094971.

Heng Li et al., "Reducing Dose Uncertainty for Spot-Scanning Proton Beam Therapy of Moving Tumors by Optimizing the Spot Delivery Sequence," International Journal of Radiation Oncology, Biology, Physics, vol. 93, Issue 3, Nov. 1, 2015, pp. 547-556, available online Jun. 18, 2015, https://doi.org/10.1016/j.ijrobp.2015.06.019.

Ion Beam Applications SA, "Netherlands Proton Therapy Center Delivers First Clinical Flash Irradiation," Imaging Technology News, May 2, 2019, Wainscot Media, https://www.itnonline.com/content/netherlands-proton-therapy-center-delivers-first-clinical-flash-irradiation.

R. M. De Kruijff, "Flash radiotherapy: ultra-high dose rates to spare healthy tissue," International Journal of Radiation Biology, 2020, vol. 96, No. 4, pp. 419-423, published online: Dec. 19, 2019, https://doi.org/10.1080/09553002.2020.1704912.

Mevion Medical Systems, "Focus on the Future: Flash Therapy," Press Releases, Sep. 16, 2019, https://www.mevion.com/newsroom/press-releases/focus-future-flash-therapy.

Joseph D. Wilson et al., "Ultra-High Dose Rate (FLASH) Radiotherapy: Silver Bullet or Fool's Gold?", Frontiers in Oncology, Jan. 17, 2020, vol. 9, Article 1563, 12 pages, doi: 10.3389/fonc.2019.01563.

David P. Gierga, "Is Flash Radiotherapy coming?", International Organization for Medical Physics, 2020, https://www.iomp.org/iomp-news2-flash-radiotherapy/.

Abdullah Muhammad Zakaria et al., "Ultra-High Dose-Rate, Pulsed (FLASH) Radiotherapy with Carbon Ions: Generation of Early, Transient, Highly Oxygenated Conditions in the Tumor Environment," Radiation Research, Dec. 1, 2020, vol. 194, Issue 6, pp. 587-593, Radiation Research Society, Published: Aug. 27, 2020, doi: https://doi.org/10.1667/RADE-19-00015.1.

(56) References Cited

OTHER PUBLICATIONS

Yusuke Demizu et al., "Carbon Ion Therapy for Early-Stage Non-Small-Cell Lung Cancer," BioMed Research International, vol. 2014, Article ID 727962, 9 pages, Hindawi Publishing Corporation, published: Sep. 11, 2014, https://doi.org/10.1155/2014/727962.

Ivana Dokic et al., "Next generation multi-scale biophysical characterization of high precision cancer particle radiotherapy using clinical proton, helium-, carbon- and oxygen ion beams," Oncotarget, Aug. 30, 2016, vol. 7, No. 35, pp. 56676-56689, published online: Aug. 1, 2016, doi: 10.18632/oncotarget.10996.

Aetna Inc., "Proton Beam, Neutron Beam, and Carbon Ion Radiotherapy," 2020, No. 0270, http://www.aetna.com/cpb/medical/data/200_299/0270.html.

Nicholas W. Colangelo et al., "The Importance and Clinical Implications of FLASH Ultra-High Dose-Rate Studies for Proton and Heavy Ion Radiotherapy," Radiat Res. Author manuscript; available in PMC Jan. 1, 2021. https://www.ncbi.nlm.nih.gov/pmc/articles/PMC6949397/ Published in final edited form as: Radiat Res. Jan. 2020; 193(1): 1-4. Published online Oct. 28, 2019. doi: 10.1667/RR15537.1.

Vincent Favaudon et al., "Ultrahigh dose-rate FLASH irradiation increases the differential response between normal and tumor tissue in mice," Science Translational Medicine, Jul. 16, 2014, vol. 6, Issue 245, 245ra93, American Association for the Advancement of Science, DOI: 10.1126/scitranslmed.3008973.

"FlashRad: Ultra-high dose-rate FLASH radiotherapy to minimize the complications of radiotherapy," 2014, https://siric.curie.fr/sites/default/files/atoms/files/flashrad.pdf.

Tami Freeman, "FLASH radiotherapy: from preclinical promise to the first human treatment," Physics World, Aug. 6, 2019, IOP Publishing Ltd, https://physicsworld.com/a/flash-radiotherapy-from-preclinical-promise-to-the-first-human-treatment/.

Intraop Medical, Inc., "IntraOp and Lausanne University Hospital Announce Collaboration in FLASH radiotherapy," Jun. 18, 2020, https://intraop.com/news-events/lausanne-university-flash-radiotherapy-collaboration/.

M.-C. Vozenin et al., "Biological Benefits of Ultra-high Dose Rate FLASH Radiotherapy: Sleeping Beauty Awoken," Clin Oncol (R Coll Radiol). Author manuscript; available in PMC Nov. 12, 2019. https://www.ncbi.nlm.nih.gov/pmc/articles/PMC6850216/ Published in final edited form as: Clin Oncol (R Coll Radiol). Jul. 2019; 31(7): 407-415. Published online Apr. 19, 2019. doi: 10.1016/j.clon.2019.04.001.

Efstathios Kamperis et al., "A FLASH back to radiotherapy's past and then fast forward to the future," J Cancer Prev Curr Res. 2019;10(6):142-144. published Nov. 13, 2019, DOI: 10.15406/jcpcr.2019.10.00407.

P. Symonds et al., "FLASH Radiotherapy: The Next Technological Advance in Radiation Therapy?", Clinical Oncology, vol. 31, Issue 7, p. 405-406, Jul. 1, 2019, The Royal College of Radiologists, Published by Elsevier Ltd., DOI: https://doi.org/10.1016/j.clon.2019.05.011.

Swati Girdhani et al., "Abstract LB-280: FLASH: A novel paradigm changing tumor irradiation platform that enhances therapeutic ratio by reducing normal tissue toxicity and activating immune pathways," Proceedings: AACR Annual Meeting 2019; Mar. 29-Apr. 3, 2019; Atlanta, GA, published Jul. 2019, vol. 79, Issue 13 Supplement, pp. LB-280, American Association for Cancer Research, DOI: https://doi.org/10.1158/1538-7445.AM2019-LB-280.

Bazalva-Carter et al., "On the capabilities of conventional x-ray tubes to deliver ultra-high (FLASH) dose rates," Med. Phys. Dec. 2019; 46 (12):5690-5695, published Oct. 23, 2019, American Association of Physicists in Medicine, doi: 10.1002/mp.13858. Epub Oct. 23, 2019. PMID: 31600830.

Manuela Buonanno et al., "Biological effects in normal cells exposed to FLASH dose rate protons," Radiother Oncol. Author manuscript; available in PMC Oct. 1, 2020. https://www.ncbi.nlm.nih.gov/pmc/articles/PMC6728238/ Published in final edited form as: Radiother Oncol. Oct. 2019; 139: 51-55. Published online Mar. 5, 2019. doi: 10.1016/j.radonc.2019.02.009.

N. Rama et al., "Improved Tumor Control Through T-cell Infiltration Modulated by Ultra-High Dose Rate Proton FLASH Using a Clinical Pencil Beam Scanning Proton System," International Journal of Radiation Oncology, Biology, Physics, vol. 105, Issue 1, Supplement , 5164-5165, Sep. 1, 2019, Mini Oral Sessions, DOI: https://doi.org/10.1016/j.ijrobp.2019.06.187.

Inserm Press Office, "Radiotherapy 'flashes' to reduce side effects," Press Release, Jul. 16, 2014, https://press.inserm.fr/en/radiotherapy-flashes-to-reduce-side-effects/13394/.

Eric S. Diffenderfer et al., "Design, Implementation, and in Vivo Validation of a Novel Proton FLASH Radiation Therapy System," International Journal of Radiation Oncology, Biology, Physics, vol. 106, Issue 2, Feb. 1, 2020, pp. 440-448, Available online Jan. 9, 2020, Published by Elsevier Inc., DOI: https://doi.org/10.1016/j.ijrobp.2019.10.049.

Valerie Devillaine, "Radiotherapy and Radiation Biology," Institut Curie, Apr. 21, 2017, https://institut-curie.org/page/radiotherapy-and-radiation-biology.

Imaging Technology News, "ProNova and medPhoton to Offer Next Generation Beam Delivery, Advanced Imaging for Proton Therapy," Oct. 6, 2014, Wainscot Media, Link: https://www.itnonline.com/content/pronova-and-medphoton-offer-next-generation-beam-delivery-advanced-imaging-proton-therapy.

Oncolink Team, "Radiation Therapy: Which type is right for me?", OncoLink Penn Medicine, last reviewed Mar. 3, 2020, Trustees of the University of Pennsylvania, https://www.oncolink.org/cancer-treatment/radiation/introduction-to-radiation-therapy/radiation-therapy-which-type-is-right-for-me.

Marco Durante et al., "Faster and safer? FLASH ultra-high dose rate in radiotherapy," Br J Radiol 2018; 91(1082): Jun. 28, 2017, British Institute of Radiology, Published Online: Dec. 15, 2017, https://doi.org/10.1259/bjr.20170628.

John R. Fischer, "PMB launches FLASH radiotherapy system for use in clinical trials," HealthCare Business News, Jun. 29, 2020, DOTmed.com, Inc., https://www.dotmed.com/news/story/51662.

Marie-Catherine Vozenin et al., "The advantage of FLASH radiotherapy confirmed in mini-pig and cat-cancer patients," Clinical Cancer Research, Author Manuscript Published OnlineFirst Jun. 6, 2018, https://clincancerres.aacrjournals.org/content/clincanres/early/2018/06/06/1078-0432.CCR-17-3375.full.pdf.

M. McManus et al., "The challenge of ionisation chamber dosimetry in ultra-short pulsed high dose-rate Very High Energy Electron beams," Sci Rep 10, 9089 (2020), published Jun. 3, 2020, https://doi.org/10.1038/s41598-020-65819-y.

Ibrahim Oraiqat et al., "An Ionizing Radiation Acoustic Imaging (iRAI) Technique for Real-Time Dosimetric Measurements for FLASH Radiotherapy," Medical Physics, vol. 47, Issue10, Oct. 2020, pp. 5090-5101, First published: Jun. 27, 2020, https://doi.org/10.1002/mp.14358.

K. Petersson et al., "Dosimetry of ultra high dose rate irradiation for studies on the biological effect induced in normal brain and GBM," ICTR-PHE 2016, p. S84, Feb. 2016, https://publisher-connector.core.ac.uk/resourcesync/data/elsevier/pdf/14c/aHR0cDovL2FwaS5IbHNIdmIlci5jb20vY29udGVudC9hcnRpY2xIL3BpaS9zMDE2Nz gxNDAxNjMwMTcyNA==.pdf.

Susanne Auer et al., "Survival of tumor cells after proton irradiation with ultra-high dose rates," Radiation Oncology 2011, 6:139, Published Oct. 18, 2011, DOI: https://doi.org/10.1186/1748-717X-6-139.

Cynthia E. Keen, "Clinical linear accelerator delivers FLASH radiotherapy," Physics World, Apr. 23, 2019, IOP Publishing Ltd, https://physicsworld.com/a/clinical-linear-accelerator-delivers-flash-radiotherapy/.

Fan et al., "Emission guided radiation therapy for lung and prostate cancers: A feasibility study on a digital patient," Med Phys. Nov. 2012; 39(11): 7140-7152. Published online Nov. 5, 2012. https://www.ncbi.nlm.nih.gov/pmc/articles/PMC3505203/ doi: 10.1118/1.4761951.

Favaudon et al., "Ultrahigh dose-rate, "flash" irradiation minimizes the side-effects of radiotherapy," Cancer / Radiotherapy, vol. 19, Issues 6-7 , Oct. 2015 , pp. 526-531, Available online Aug. 12, 2015, https://doi.org/10.1016/j.canrad.2015.04.006.

(56) References Cited

OTHER PUBLICATIONS

O. Zlobinskaya et al., "The Effects of Ultra-High Dose Rate Proton Irradiation on Growth Delay in the Treatment of Human Tumor Xenografts in Nude Mice," Radiation Research, 181(2):177-183. Published Feb. 13, 2014, DOI: http://dx.doi.org/10.1667/RR13464.1.

Bjorn Zackrisson, "Biological Effects of High Energy Radiation and Ultra High Dose Rates," Umea University Medical Dissertations, New series No. 315—ISSN 0346-6612, From the Department of Oncology, University of Umea, Umea, Sweden, ISBN 91-7174-614-5, Printed in Sweden by the Printing Office of Umea University, Umea, 1991.

P. Montay-Gruel et al., "Irradiation in a flash: Unique sparing of memory in mice after whole brain irradiation with dose rates above 100 Gy/s," Radiotherapy and Oncology, vol. 124, Issue 3, Sep. 2017, pp. 365-369, Available online May 22, 2017, doi: 10.1016/j.radonc.2017.05.003.

BW Loo et al., "Delivery of Ultra-Rapid Flash Radiation Therapy and Demonstration of Normal Tissue Sparing After Abdominal Irradiation of Mice," International Journal of Radiation Oncology, Biology, Physics, vol. 98, Issue 2, p. E16, Supplement: S Meeting Abstract: P003, Published: Jun. 1 2017, DOI: https://doi.org/10.1016/j.ijrobp.2017.02.101.

Bhanu Prasad Venkatesulu et al., "Ultra high dose rate (35 Gy/sec) radiation does not spare the normal tissue in cardiac and splenic models of lymphopenia and gastrointestinal syndrome," Sci Rep 9, 17180 (2019), Published Nov. 20, 2019, DOI: https://doi.org/10.1038/s41598-019-53562-y.

P. Montay-Gruel et al., "Long-term neurocognitive benefits of FLASH radiotherapy driven by reduced reactive oxygen species," PNAS May 28, 2019, vol. 116, No. 22, pp. 10943-10951; first published May 16, 2019, https://doi.org/10.1073/pnas.1901777116.

Peter G. Maxim et al., "FLASH radiotherapy: Newsflash or flash in the pan?", Medical Physics, 46 (10), Oct. 2019, pp. 4287-4290, American Association of Physicists in Medicine, First published: Jun. 27, 2019, https://doi.org/10.1002/mp.13685.

Andrei Pugachev et al., "Pseudo beam's-eye-view as applied to beam orientation selection in intensity-modulated radiation therapy," Int. J. Radiation Oncology Biol. Phys., vol. 51, Issue 5, p. 1361-1370, Dec. 1, 2001, DOI: https://doi.org/10.1016/S0360-3016(01)01736-9.

Xiaodong Zhang et al., "Intensity-Modulated Proton Therapy Reduces the Dose to Normal Tissue Compared With Intensity-Modulated Radiation Therapy or Passive Scattering Proton Therapy and Enables Individualized Radical Radiotherapy for Extensive Stage IIIB Non-Small-Cell Lung Cancer: A Virtual Clinical Study," Int. J. Radiation Oncology Biol. Phys., vol. 77, No. 2, pp. 357-366, 2010, Available online Aug. 5, 2009, DOI: https://doi.org/10.1016/j.ijrobp.2009.04.028.

A. J. Lomax et al, "Intensity modulated proton therapy: A clinical example," Medical Physics, vol. 28, Issue 3, Mar. 2001, pp. 317-324, First published: Mar. 9, 2001, https://doi.org/10.1118/1.1350587.

Lamberto Widesott et al., "Intensity-Modulated Proton Therapy Versus Helical Tomotherapy in Nasopharynx Cancer: Planning Comparison and NTCP Evaluation," Int. J. Radiation Oncology Biol. Phys., vol. 72, No. 2, pp. 589-596, Oct. 1, 2008, Available online Sep. 13, 2008, DOI: https://doi.org/10.1016/j.ijrobp.2008.05.065.

Andrei Pugachev et al., "Role of beam orientation optimization in intensity-modulated radiation therapy," Int. J. Radiation Oncology Biol. Phys., vol. 50, No. 2, pp. 551-560, Jun. 1, 2001, Available online May 10, 2001, DOI: https://doi.org/10.1016/S0360-3016(01)01502-4.

Damien C. Weber et al., "Radiation therapy planning with photons and protons for early and advanced breast cancer: an overview," Radiat Oncol. 2006; 1: 22. Published online Jul. 20, 2006, doi: 10.1186/1748-717X-1-22.

RaySearch Laboratories, "Leading the way in cancer treatment, Annual Report 2013," RaySearch Laboratories (publ), Stockholm, Sweden, 94 pages, Apr. 2014, https://www.raysearchlabs.com/siteassets/about-overview/media-center/wp-re-ev-n-pdfs/brochures/raysearch-ar-2013-eng.pdf.

Fredrik Carlsson, "Utilizing Problem Structure in Optimization of Radiation Therapy," KTH Engineering Sciences, Doctoral Thesis, Stockholm, Sweden, Apr. 2008, Optimization and Systems Theory, Department of Mathematics, Royal Institute of Technology, Stockholm, Sweden, ISSN 1401-2294, https://www.raysearchlabs.com/globalassets/about-overview/media-center/wp-re-ev-n-pdfs/publications/thesis-fredrik_light.pdf.

Chang-Ming Charlie MA, "Physics and Dosimetric Principles of SRS and SBRT," Mathews J Cancer Sci. 4(2): 22, 2019, published: Dec. 11, 2019, ISSN: 2474-6797, DOI: https://doi.org/10.30654/MJCS.10022.

Alterego-admin, "Conventional Radiation Therapy May Not Protect Healthy Brain Cells," International Neuropsychiatric Association—INA, Oct. 10, 2019, https://inawebsite.org/conventional-radiation-therapy-may-not-protect-healthy-brain-cells/.

* cited by examiner

SYSTEM AND METHOD FOR BIOLOGICAL TREATMENT PLANNING AND DECISION SUPPORT

FIELD

Embodiments of the present invention generally relate to the field of radiotherapy. More specifically, embodiments of the present invention relate to computer-implemented treatment planning methods and systems for radiotherapy treatment.

BACKGROUND

Radiotherapy treatment planning based on biological parameters is referred to in the art as biological planning. One goal of radiotherapy treatment and biological planning is to maximize the dose supplied to a target tumor while minimizing the dose absorbed by the surrounding (normal) tissue. Treatment outcome regarding tumor control and normal tissue toxicities not only depend on physical parameters, such as dose, but also depend on a multitude of biological parameters that may or may not be known at the time of treatment.

Radiotherapy treatment planning typically involves extracting data from in vitro experiments where cell lines are irradiated, and the cell survival curves are used to define alpha-beta ratios of different cell types. Probabilistic models of tumor control probability (TCP) and normal tissue complication probability (NTCP) are created and can be used for clinical decision making. However, the clinical relevance of TCP/NTCP models is uncertain and there is a low level of confidence in the community regarding the accuracy of the models and the predicted values thereof. Moreover, it remains unclear which biological inputs might be required in order to achieve effective biological planning and to support a decision to treat a specific patient in a specific manner.

Currently the inclusion of biological parameters in treatment planning and decision making is not integrated into treatment planning systems. Treatment plans are often solely based on physical dose and displayed in 3D. Any relevant biological knowledge correlating treatment plans to outcome is not evaluated or is achieved separately from plan quality dosimetry metrics. For example, most clinics only use dosimetric endpoint goals as a proxy for biological impact, such as, "do not exceed max spinal cord dose of x."

In order to use biological information to guide treatment decision using current techniques, physically recorded parameters, such as dose, have to be extracted from the treatment planning system, and outcome modeling must be built in-house separately for each research parameter that is under evaluation. This has resulted in several biological models for radiation therapy developed for research, none of which are clinically accepted for use in actual treatment planning. Moreover, the dose is typically visualized with a color wash map; however, there is currently no built-in display method to visualize user-defined biological input functions in a similar fashion.

For clinical research and clinical trials, there are very few tools that can allow a researcher to test biological models that correlate input (4-D physically measured/"known" quantities) in relation to the output (e.g., biological observables such as toxicities, cell damage as observed on a 3D computerized tomography (CT), or even patient reported outcomes). Additionally, there are few tools that allow the user to compile the inputs in a reasonable fashion for radiotherapy. One common problem is that users do not know which treatment plan to apply to a registry because different versions of the treatment plan may be adapted and modified over time. For example, one treatment plan (including the 3D dose distribution) can represent a snapshot of how the dose is deposited given a certain beam arrangement and/or beam parameters on the patient's anatomy at the moment the simulation CT was acquired. Therefore, the treatment plan and the dosimetric endpoints often serve the registry as the input, but this input entails a large degree of uncertainty.

In many cases, radiation can be delivered to the tumor with submillimeter precision while mostly sparing normal tissue, ultimately leading to tumor cell killing. However, the tumor cell's ability to escape the cell killing effects of radiation and/or to develop resistance mechanism can counteract the tumor cell killing action of radiotherapy, potentially limiting the therapeutic effect of radiotherapy to treat cancer. Furthermore, the potential for normal tissue toxicity can impact the therapeutic window of radiation therapy as a treatment paradigm. Delivery of ultra-high dose radiation is believed to spare normal tissue from radiation-induced toxicity, thus increasing the therapeutic window. However, the therapeutic window can be widened even more by combining ultra-high dose radiation with targeted drugs, or the use of biomarkers for patient stratification.

SUMMARY OF THE INVENTION

Embodiments of the present invention provide integrated solutions to radiotherapy treatment planning that enable accurate recording and accumulation of physical parameters as input (e.g., dose, dose rate, irradiation time per voxel, etc.). User-defined functions are evaluated to correlate the input parameters with 4D biological outcomes. The resulting biological parameters can be visualized on a computer display as a biological outcome map to evaluate decisions, support decisions, and optimize decisions regarding the parameters of the radiotherapy treatment plan, for example, for supporting clinical trials and related clinical research. Including biological information into the treatment planning system leads to biologically optimized treatment capable of using ultra-high dose radiation. Biological parameters can be included into treatment planning on a voxel by voxel basis and the results can be displayed as a biological map.

According to one embodiment, a computer-implemented method for radiotherapy treatment planning is disclosed. The method includes receiving physical input parameters, evaluating a treatment hypothesis to determine a relationship between the physical input parameters and a biological outcome, generating a biological outcome map using an input function based on the relationship, displaying the biological outcome map on a display device to visualize the relationship, and optimizing a radiotherapy treatment plan based on the relationship depicted in the biological outcome map.

According to some embodiments, the input function represents a biological model.

According to some embodiments, optimizing the radiotherapy treatment plan includes minimizing a dose delivered to normal tissue.

According to some embodiments, the computer-implemented method includes determining the biological outcome by analyzing a post-treatment image.

According to some embodiments, optimizing the radiotherapy treatment plan includes optimizing a physical dose and a biological dose of the radiotherapy treatment plan, and the method further includes assigning priority levels to the physical dose and the biological dose.

According to some embodiments the displaying the biological outcome map includes overlaying the biological outcome map on top of a 3D dose map.

According to some embodiments the biological outcome map includes a 3D image.

According to some embodiments the biological outcome map includes a 4D image that varies over time.

According to some embodiments the receiving physical input parameters includes accumulating the physical input parameters as 4D physical measurements.

According to some embodiments the physical input parameters are associated with voxels.

According to some embodiments the physical input parameters include at least one of a dose and a dose rate.

According to some embodiments the physical input parameters include at least one of an irradiation time and a beam overlap.

According to some embodiments the biological outcome includes a toxicity level.

According to some embodiments the biological outcome includes at least one of a systemic biomarker and a genetic biomarker. Some embodiments include at least one of a hypofractionated and split flash regimen, where the regimen comprises a duty cycle optimized for timescales associated with disease presentation, cancer location, cellular lifecycle, and immune response times.

According to another embodiment, a system for radiotherapy treatment planning is disclosed. The system includes a display, a memory and a processor in communication with the memory that executes instructions for performing a method of radiotherapy treatment planning. The method includes receiving physical input parameters, evaluating a treatment hypothesis to determine a relationship between the physical input parameters and a biological outcome, generating a biological outcome map using an input function based on the relationship, displaying the biological outcome map on a computer-controlled display device to visualize the relationship, and optimizing a radiotherapy treatment plan based on the relationship depicted in the biological outcome map.

According to another embodiment, a non-transitory computer-readable storage medium embodying instructions that are executed by a processor to cause the processor to perform a method of radiotherapy treatment planning is disclosed. The method includes receiving physical input parameters, evaluating a treatment hypothesis to determine a relationship between the physical input parameters and a biological outcome, generating a biological outcome map using an input function based on the relationship, displaying the biological outcome map on a computer-controlled display device to visualize the relationship, and optimizing a radiotherapy treatment plan based on the relationship depicted in the biological outcome map.

BRIEF DESCRIPTION OF THE DRAWINGS

The accompanying drawings, which are incorporated in and form a part of this specification and in which like numerals depict like elements, illustrate embodiments of the present disclosure and, together with the description, serve to explain the principles of the disclosure.

DETAILED DESCRIPTION

Figure 1:
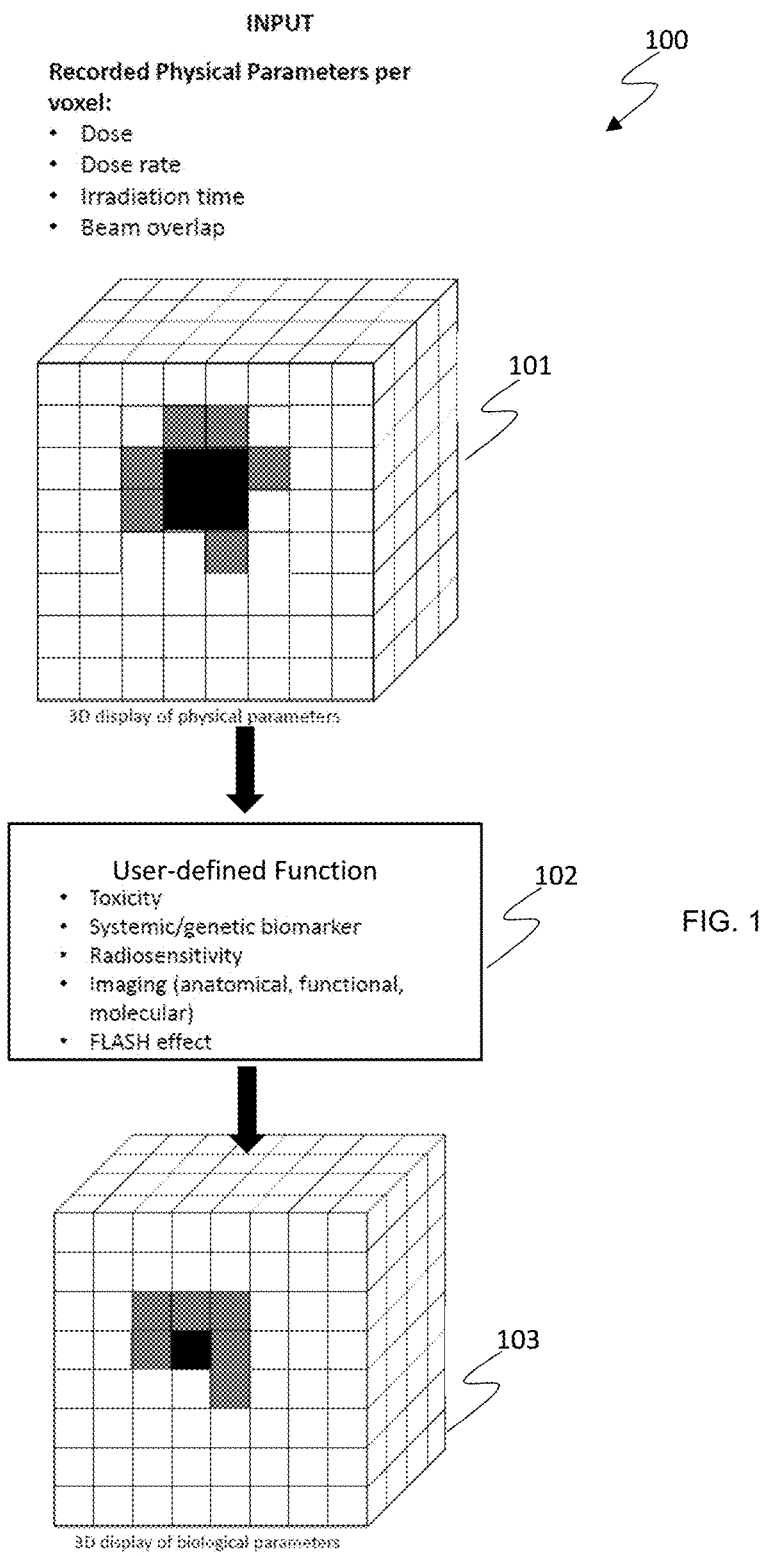
FIG. 1 is a diagram of an exemplary physical parameter input map and a resultant biological outcome map generated according to a user-defined function or model depicted according to embodiments of the present invention.

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known methods, procedures, components, and circuits have not been described in detail as not to unnecessarily obscure aspects and features of the subject matter.

Some embodiments may be described in the general context of computer-executable instructions, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Portions of the detailed description that follows are presented and discussed in terms of a method. Although steps and sequencing thereof are disclosed in a figure herein (e.g., FIG. 2) describing the operations of this method, such steps and sequencing are exemplary. Embodiments are well suited to performing various other steps or variations of the steps recited in the flowchart of the figure herein, and in a sequence other than that depicted and described herein.

Some portions of the detailed description are presented in terms of procedures, steps, logic blocks, processing, and other symbolic representations of operations on data bits that can be performed on computer memory. These descriptions and representations are the means used by those skilled in the data processing arts to most effectively convey the substance of their work to others skilled in the art. A procedure, computer-executed step, logic block, process, etc., is here, and generally, conceived to be a self-consistent sequence of steps or instructions leading to a desired result. The steps are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout, discussions utilizing terms such as "accessing," "displaying," "writing," "including," "storing," "transmitting," "traversing," "determining," "identifying," "observing," "adjusting," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

System and Method for Biological Treatment Planning and Decision Support

Embodiments of the present invention provide integrated solutions to radiotherapy treatment planning that enable accurate recording and accumulation of physical parameters as input (e.g., dose, dose rate, irradiation time per voxel, etc.). User-defined functions based on biological models are evaluated to correlate the input parameters with biological outcomes for biological planning. The biological parameters can be visualized on a computer screen as a biological outcome map to evaluate decisions, provide decision support, and optimize decisions regarding the parameters of a radiotherapy treatment plan, for example, for supporting clinical trials and related clinical research. Embodiments of the present invention can provide decision support for clinical trials by determining which arm of a trial a group of patients should be assigned to based on physical input parameters, such as elevated biomarkers, and by tracking the outcome results of the group of patients over time to evaluate a clinical research hypothesis.

A radiobiological equivalent (RBE) dose is a metric that takes biological parameters derived from experiments into consideration and modifies the dose by a specific factor. The modified dose then becomes the RBE dose and can be used for treatment planning and optimizations. Embodiments of the present invention advantageously enable treatment plans to be generated based on how the dose is affected by biological factors in addition to dosimetry. Moreover, embodiments of the present invention can be used as a research tool for evaluating various endpoints in addition to dose for clinical research and hypothesis evaluation. According to some embodiments, a software tool is executed by a computer system that takes known physical parameters as input, such as dose, per-voxel radiation time, and allows a user to test a clinical research hypothesis using the computer system. For example, a user can use the software tool to correlate the time a voxel has been irradiated with the toxicity in the voxel, and the result can be displayed on a computer screen as a 4D biological outcome map.

Embodiments of the present invention can evaluate a post-treatment image automatically using a computer system, where voxels of 3D physical parameters map are assigned toxicity scores based according to a hypothesis or biological model. Thereafter, the relationship (e.g., correlation) between the input and output, such as irradiation time and toxicity, can be visualized and/or quantified by rendering an image or video on a display device of the computer system. For example, the relationship can be used to define a function or model for generating a 3D map to visualize the relationship and assist treatment planning and optimization based on the correlated metric (e.g., irradiation time), in addition to a conventional dose map. According to some embodiments, the relationship between input and output is visualized as a 4D video map that includes a 3D image that changes over time. A time component is evaluated to generate the 4D video map of events occurring over time, and the 4D video is rendered on a display device of the computer system.

According to some embodiments, biological parameters for a treatment plan are defined on a per-voxel basis using a treatment planning tool, and a biological outcome map is generated according to a function or model and displayed to the user. Tumor control probability (TCP) planning and normal tissue complication probability (NTCP) planning generated in this way may include any user-defined biological parameters relevant to treatment planning in an integrated system, and the metric is rendered in 3D or 4D to track plan adaptions and accumulate the actual delivered dose. In this way, the user can automatically visualize and quantify relationships and/or correlations arising from research hypotheses and support treatment planning and optimization decisions using the computer-implemented treatment planning tool.

Moreover, the treatment planning tool disclosed herein can track or receive known 3D doses calculated during a simulation phase and overlay or otherwise visualize biological models to perform biological evaluation based on the calculated doses. The tool can simultaneously optimize physical dose and biological dose and determine the priority to assign to either biology or the physical dose. In this way, the computer-implemented tool can evaluate biological models in the treatment planning evaluation stage and incorporate biological factors into the plan optimization process. For example, biological planning can be layered on top of the physical dose optimization to visualize the relationship between input and output.

According to some embodiments, radiation treatment is combined with immune modulators to improve both the efficacy of radiation—both locally and systemically—as well as the efficacy of immune modulators. The radiation-immune modulator combination approach may require delivery of an ultra-high dose radiation to the tumor, knowledge of optimal dosing and sequence based on the immune modulators mechanism of action, fractionation pattern, and location of the primary tumor to ultimately achieve an optimal response. Furthermore, ultra-high dose radiation may facilitate the infiltration of immune cells deep into the core of the tumor, thus converting an immune desert into an immunological active tumor, thus potentially improving the efficacy of immune modulatory approaches. For example, radiation-induced tumor cell death leads to release of tumor antigens from lysed cells, increased MHC-1 expression on antigen presenting cells, and enhanced diversity of the intratumoral T-cell population. These factors (among others) are key to initiate activation of the body's own immune systems to eradicate cancer cells. Immune modulators are being explored to activate the body's own immune system, but are known to have limitations as monotherapy (e.g. response rate in patients). Therefore, embodiments of the present invention can incorporate check point inhibitors, co-stimulators, broad immune modulators, and chemokine inhibitors, and inhibitors of macrophage migration, for example.

With regard to FIG. 1, a diagram 100 of an exemplary physical parameter input map 101 and a resultant biological outcome map 103 generated according to a user-defined function or model 102 (e.g., clinical hypothesis) is depicted according to embodiments of the present invention. Such maps can be realized as data stored in computer memory and rendered for visualization by a computer on a display or printer. Embodiments of the present invention enable the accumulation of input data in a more accurate fashion compared to typical research hypothesis testing, where users must first extract physical parameters from a tissue polypeptide specific antigen (TPS) and build custom code in a different environment for testing the research hypothesis, for identifying important correlations, and for inputting the data back into the TPS. The input data 101 can include, but is not limited, to 3D input data such as dose accumulation from daily dose calculations based on cone beam computed tomography (CBCT), dose accumulation from plan adaptations, irradiation time per voxel accumulation, cumulative dose rate per voxel, and beam overlap per voxel, for example. Voxel-based treatment planning may be performed based on the correlation of 3D voxel recording of physical parameters (e.g., dose, dose rate, irradiation time) to 3D-voxel based output. Input data that is not 3D, such as tumor size, patient-reported outcome, survival, local control, biomarkers, patient medical history and demographic information, previous radiotherapy treatment data, cellular/biological timescales associated with disease presentation, cancer location, and cellular lifecycle (e.g., radiosensitivity) may also be included in the input data 101. The input data 101 can be entered manual by a user, or automatically entered by the computer system according to a treatment plan or physical metrics tracked by a radiation therapy system.

The user-defined function or model 102 is used to generate the biological outcome map based on a relationship (e.g., correlation) between the physical parameter input and a biological outcome on a per-voxel basis. For example, the user-defined function 102 can be based on a biological model representing the relationship between irradiation time and toxicity (e.g., the toxicity increases over time in correlation with irradiation time), higher dosage rates correlated with lower toxicity, and higher levels of biomarkers correlated with increased global radio sensitivity. Moreover, embodiments of the present invention enable the output data 103 to be stored more accurately compared to traditional techniques. For example, toxicities over time can be stored along with computerized tomography (CT)/magnetic resonance imaging (MRI)/positron emission tomography (PET) based cellular damage and tumor response per voxel. Advantageously, embodiments of the present invention enable accurate inputs 101 to be correlated with accurate outputs 103 based on biological models of user-defined functions 102. The user-defined functions 102 can be based on toxicity, systemic or genetic biomarkers, radio sensitivity, imaging information (anatomical, functional, molecular), and Flash effect, for example.

Figure 2:
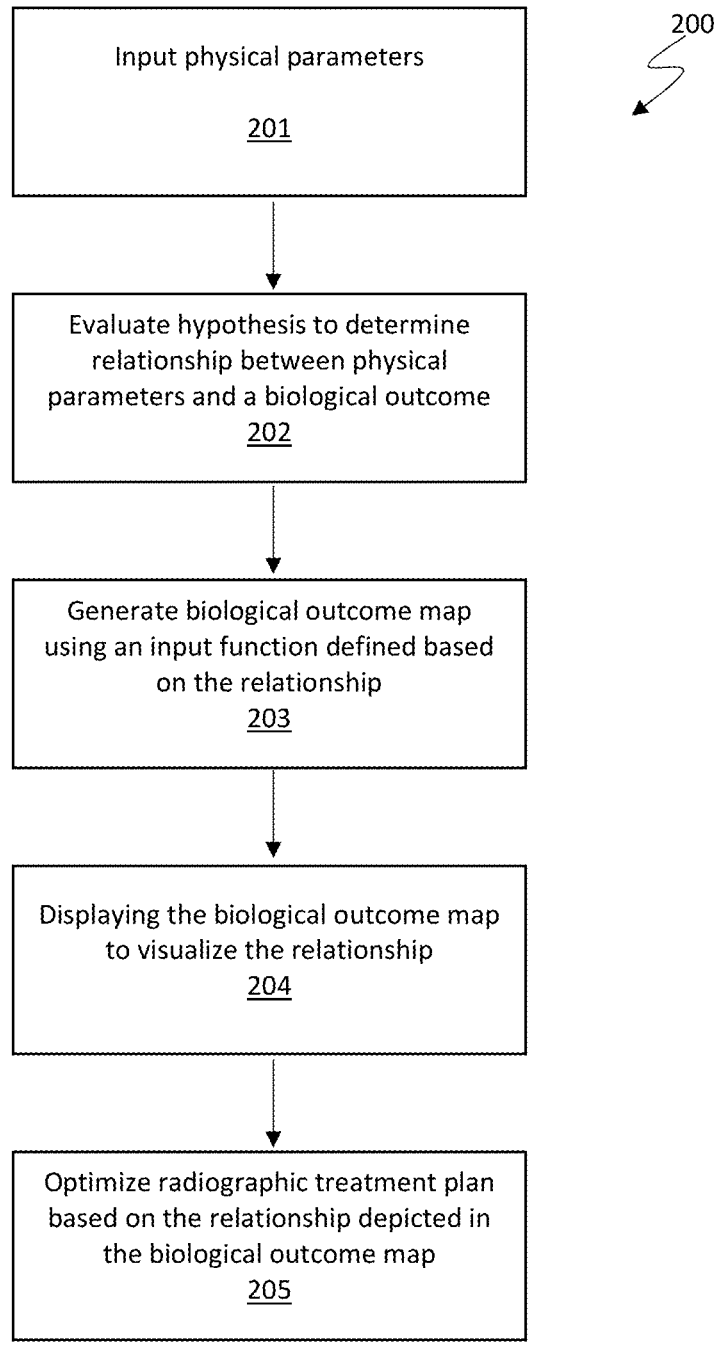
FIG. 2 is a flowchart depicting an exemplary sequence of computer implemented steps for performing biological planning based on physical input parameters and a biological model according to embodiments of the present invention.

With regard to FIG. 2, an exemplary sequence of computer implemented steps to realize process 200 for performing biological planning based on physical input parameters and a biological model is depicted according to embodiments of the present invention. The steps may be realized as program code stored in memory and executed by a computer processor. At step 201, recorded physical parameters are received as input. The physical parameters may include a recorded dose, a dose rate, an irradiation time, and/or a beam overlap, for example, and the physical parameters may be associated with voxels of a treatment map. According to some embodiments, step 201 includes recording/accumulating physical input parameters over time, such as dose accumulation, irradiation time per voxel accumulation, and/or cumulative dose rate per voxel. The input data can be entered manual by a user, or automatically entered by a computer system according to a treatment plan or physical metrics tracked by a radiation therapy system.

At step 202, a hypothesis (e.g., a clinical research hypothesis) is tested to correlate input parameters with a biological parameter or outcome. For example, step 202 can include correlating the irradiation time of a voxel with the toxicity level (outcome) of the voxel. According to some embodiments, the biological outcome is determined by evaluating post-treatment images or other data. For example, radiomic techniques known in the art may be used to automatically associate the post-treatment image with biological outcome values for evaluating the hypothesis or model.

At step 203, a biological outcome map is generated to assign each voxel of the treatment map with a value (e.g., a toxicity score) based on an input function representing a biological model. At step 204, the biological outcome map is displayed on a display device to visualize the relationship (e.g., correlation) between the input parameter and the biological parameter or outcome. For example, the biological outcome map can be overlaid on top of a 3D dose map to visualize the relationship and differences between the biological outcome map and the 3D dose map. According to some embodiments, a time component is included at step 204 to generate a 4D video map of the events occurring over time. At step 205, the treatment planning process is optimized based on the correlation depicted in the biological outcome map. According to some embodiments, optimizing the radiotherapy treatment plan includes optimizing or adjusting a physical dose and a biological dose of the radiotherapy treatment plan. Moreover, some embodiments further assign priority levels to the physical dose and the biological dose based on the biological outcome map.

Exemplary Computer System

Embodiments of the present invention are drawn to computer systems for planning and optimizing a radiotherapy treatment plan by visualizing and quantifying correlations arising from tested hypotheses. The following discussion describes such exemplary computer systems.

Figure 3:
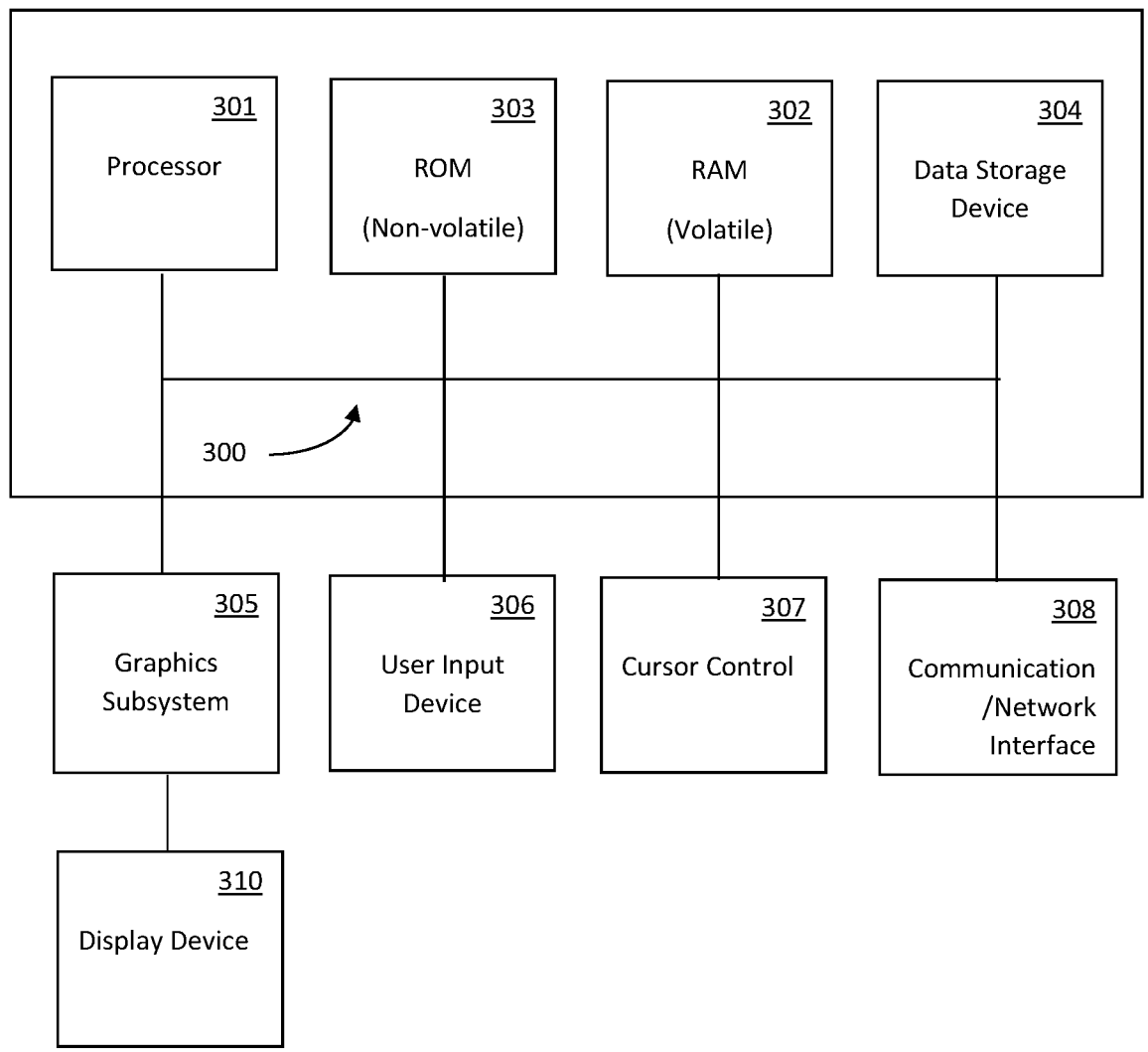
FIG. 3 is a block diagram depicting an exemplary computer system upon which embodiments of the present invention can be implemented.

In the example of FIG. 3, the exemplary computer system 312 includes a central processing unit (CPU) 301 for running software applications (e.g., a workload management application) and optionally an operating system. Random access memory 302 and read-only memory 303 store applications and data for use by the CPU 301. Data storage device 304 provides non-volatile storage for applications and data and may include fixed disk drives, removable disk drives, flash memory devices, and CD-ROM, DVD-ROM or other optical storage devices. The optional user inputs 306 and 307 comprise devices that communicate inputs from one or more users to the computer system 312 (e.g., mice, joysticks, cameras, touch screens, and/or microphones).

A communication or network interface 308 allows the computer system 312 to communicate with other computer systems, networks, or devices via an electronic communications network, including wired and/or wireless communication and including an Intranet or the Internet. The display device 310 may be any device capable of displaying visual information in response to a signal from the computer system 312 and may include a flat panel touch sensitive display, for example. The components of the computer system 312, including the CPU 301, memory 302/303, data storage 304, user input devices 306, and graphics subsystem 305 may be coupled via one or more data buses 300.

In the embodiment of FIG. 3, a graphics subsystem 305 is optional and may be coupled with the data bus and the components of the computer system 312. The graphics system 305 may comprise a physical graphics processing unit (GPU) and graphics/video memory. GPU may include one or more rasterizers, transformation engines, and geometry engines, and generates pixel data from rendering commands to create output images. The physical GPU can be configured as multiple virtual GPUs that may be used in parallel (e.g., concurrently) by a number of applications or processes executing in parallel, or multiple physical GPUs may be used simultaneously. Graphics subsystem 305 can output display data to display device 310, for example, to visualize correlations and/or differences between biological outcomes of a tested hypothesis rendered in 3D and a 3D dose map as discussed above.

Embodiments of the present invention are thus described. While the present invention has been described in particular embodiments, it should be appreciated that the present invention should not be construed as limited by such embodiments, but rather construed according to the following claims.

What is claimed is:

1. A computer-implemented method for radiotherapy treatment planning, the method comprising:
   receiving physical input parameters comprising a physical input parameter for each voxel of a plurality of voxels of a treatment map;
   generating a biological outcome map to assign to said each voxel of the treatment map a respective value determined using an input function that is based on a relationship between the physical input parameter for said each voxel and a biological outcome for said each voxel;
   displaying the biological outcome map on a computer controlled display device to visualize the relationship in a displayed biological outcome map, wherein the displayed biological outcome map displays a respective biological outcome for said each voxel; and
   optimizing a radiotherapy treatment plan based on the relationship depicted in the biological outcome map.

2. The method as described in claim 1 wherein the input function represents a computer memory resident biological model.

3. The method as described in claim 1 wherein optimizing the radiotherapy treatment plan comprises reducing a dose delivered to normal tissue.

4. The method as described in claim 1 further comprising determining the biological outcome by analyzing a post-treatment image.

5. The method as described in claim 1 wherein optimizing the radiotherapy treatment plan comprises optimizing a physical dose and a biological dose of the radiotherapy treatment plan, and further comprising assigning priority levels to the physical dose and the biological dose.

6. The method as described in claim 1 wherein the displaying the biological outcome map comprises overlaying the biological outcome map on top of a 3D dose map in a rendering of the display device.

7. The method as described in claim 1 wherein the biological outcome map comprises a 3D image.

8. The method as described in claim 1 wherein the biological outcome map comprises a 4D image that varies over time.

9. The method as described in claim 8 wherein the receiving physical input parameters comprises accumulating the physical input parameters as 4D physical measurements.

10. The method as described in claim 1 wherein the physical input parameters comprise at least one of a dose and a dose rate.

11. The method as described in claim 1 wherein the physical input parameters comprise at least one of an irradiation time and a beam overlap.

12. The method as described in claim 1 wherein the biological outcome comprises a toxicity level.

13. The method as described in claim 1 wherein the biological outcome comprises at least one of a systemic biomarker and a genetic biomarker.

14. An electronic system for radiotherapy treatment planning, the system comprising:
   a display device;
   a memory; and
   a processor in communication with the memory wherein the processor is operable to execute instructions for performing a method of radiotherapy treatment planning, the method comprising:
      receiving physical input parameters comprising a physical input parameter for each voxel of a plurality of voxels of a treatment map;
      generating a biological outcome map in the memory to assign to said each voxel a respective value determined using an input function that is based on a relationship between the physical input parameter for said each voxel and a biological outcome for said each voxel;
      displaying the biological outcome map on the display device to visualize the relationship in a displayed biological outcome map, wherein the displayed biological outcome map displays a respective biological outcome for said each voxel; and
      optimizing a radiotherapy treatment plan based on the relationship depicted in the biological outcome map.

15. The system as described in claim 14 wherein the input function represents a biological model.

16. The system as described in claim 14 wherein optimizing the radiotherapy treatment plan comprises reducing a dose delivered to normal tissue.

17. The system as described in claim 14 wherein the method further comprises determining the biological outcome by analyzing a post-treatment image.

18. The system as described in claim 14 wherein optimizing the radiotherapy treatment plan comprises optimizing a physical dose and a biological dose of the radiotherapy treatment plan, and wherein the method further comprises assigning priority levels to the physical dose and the biological dose.

19. The system as described in claim 14 wherein the displaying the biological outcome map comprises overlaying the biological outcome map on top of a 3D dose map in a rendering on the display device.

20. The system as described in claim 14 wherein the biological outcome map comprises a 3D image.

21. The system as described in claim 14 wherein the biological outcome map comprises a 4D image that varies over time.

22. The system as described in claim 21 wherein the receiving physical input parameters comprises accumulating the physical input parameters as 4D physical measurements.

23. The system as described in claim 14 wherein the physical input parameters comprise at least one of a dose and a dose rate.

24. The system as described in claim 14 wherein the physical input parameters comprise at least one of an irradiation time and a beam overlap.

25. The system as described in claim 14 wherein the biological outcome comprises a toxicity level.

26. The system as described in claim 14 wherein the biological outcome comprises at least one of a systemic biomarker and a genetic biomarker.

27. The system as described in claim 14 wherein the method further comprises at least one of a hypofractionated and split flash regimen, wherein the regimen comprises a duty cycle optimized for timescales associated with disease presentation, cancer location, cellular lifecycle, and immune response times.

28. A non-transitory computer-readable storage medium embodying instructions that are executed by a processor to cause the processor to perform a method of radiotherapy treatment planning, the method comprising:

accumulating physical input parameters comprising a physical input parameter for each voxel of a plurality of voxels of a treatment map;

generating a biological outcome map to assign to said each voxel of the treatment map a respective value determined using an input function that is based on a relationship between the physical input parameter for said each voxel and a biological outcome for said each voxel;

displaying the biological outcome map on a display device to visualize the relationship in a displayed biological outcome map, wherein the displayed biological outcome map displays a respective biological outcome for said each voxel; and optimizing a radiotherapy treatment plan based on the relationship depicted in the biological outcome map.

* * * * *